United States Patent [19]

Inoue et al.

[11] 4,331,569
[45] May 25, 1982

[54] SUBSTITUTED NORBORNANONE ACETALS, PROCESS FOR PREPARING THE SAME, AND PERFUME COMPOSITIONS CONTAINING THE SAME

[75] Inventors: Yoshiharu Inoue, Ohsaka; Fumio Tanimoto, Kyoto; Hisao Kitano, Ohsaka, all of Japan

[73] Assignee: Nippon Petrochemicals Co., Ltd., Japan

[21] Appl. No.: 220,528

[22] Filed: Dec. 29, 1980

[30] Foreign Application Priority Data

Dec. 29, 1979 [JP] Japan .................................. 54-172063
Feb. 21, 1980 [JP] Japan .................................. 55-6060
May 13, 1980 [JP] Japan .................................. 55-63116
May 14, 1980 [JP] Japan .................................. 55-63677

[51] Int. Cl.³ .................... A61K 7/46; C07D 319/04; C07D 317/10
[52] U.S. Cl. ................................ 252/522 R; 549/336
[58] Field of Search .................. 260/340.9 R, 340.7, 260/338; 252/522 R

[56] References Cited

U.S. PATENT DOCUMENTS

3,634,499 1/1972 Loeffler .................. 260/340.9 R
3,679,756 7/1972 Kretschmar et al. ........ 260/340.9 R
3,748,344 7/1973 McCloud et al. ............ 260/340.9 R
3,860,635 1/1975 Kitchens ........................ 252/522 R

*Primary Examiner*—Ethel G. Love
*Attorney, Agent, or Firm*—Ostrolenk, Faber, Gerb & Soffen

[57] ABSTRACT

The substituted norbornanones represented by general formula (I):

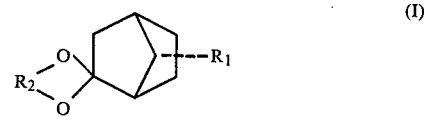

(wherein $R_1$ is an alkenyl group having 2 or 3 carbon atoms or an alkylidene group having 1 to 3 carbon atoms and $R_2$ is a saturated hydrocarbon group having 2 to 7 carbon atoms with the dotted line between the two carbon atoms indicating a single bond when $R_1$ is an alkenyl group and a double bond when $R_1$ is an alkylidene group) are useful for perfume compositions. The substituted norbornanones represented by the general formula (I) may be prepared from the corresponding alkenyl or alkylidene norbornanones with diols in the presence of an acid catalyst.

18 Claims, No Drawings

SUBSTITUTED NORBORNANONE ACETALS, PROCESS FOR PREPARING THE SAME, AND PERFUME COMPOSITIONS CONTAINING THE SAME

BACKGROUND OF THE INVENTION

1. Field of the Invention

The present invention relates to novel derivatives of substituted norbornanones, specifically, alkenyl norbornanones or alkylidene norbornanones, a process for preparing the same, and a perfume composition containing the same.

2. Deccription of the Prior Art

A variety of compounds having the norbornane ring have been heretofore prepared. For example, U.S. Pat. No. 3,860,635 discloses a process for preparing vinyl norbornanones. Similarly, U.S. Pat. No. 3,748,344 discloses a process for preparing cyclic acetals of norbornane carboxyaldehydes.

SUMMARY OF THE INVENTION

It has been found that alkenyl or alkylidene norbornanones can be reacted with diols to give novel acetal compounds which have pleasant fragrances and are useful as components for providing the fragrance of a perfume, and that their acetal compounds can be employed effectively as intermediate compounds for organic synthesis and as raw materials for synthetic resins by utilizing an unsaturated group such as the ethylidene group or the vinyl group. The present invention was completed on the basis of this finding.

Thus, the present invention includes compounds represented by the following general formula:

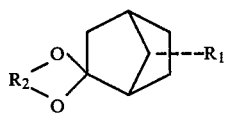

(I)

(wherein $R_1$ is an alkenyl group having 2 or 3 carbon atoms or an alkylidene group having 1 to 3 carbon atoms, and $R_2$ is a saturated hydrocarbon group having 2 to 7 carbon atoms, with the dotted line between the two carbon atoms indicating a single bond when $R_1$ in an alkenyl group and a double bond when $R_1$ is an alkylidene group); a process for preparing the compounds represented by the above general formula (I) characterized by reacting an alkenyl or alkylidene norbornanone with a diol in the presence of an acid catalyst at a temperature of 10° C. to 150° C.; and a perfume composition containing the compounds represented by the general formula (I).

DETAILED DESCRIPTION OF THE PREFERRED EMBODIMENTS

The alkenyl or alkylidene norbornanones to be used for the process in accordance with the present invention may be represented by general formula (VI):

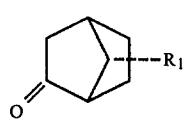

(VI)

(wherein $R_1$ is an alkenyl group having 2 or 3 carbon atoms or an alkylidene group having 1 to 3 carbon atoms, with the dotted line between the carbon atoms indicating a single bond when $R_1$ is an alkenyl group and a double bond when $R_1$ is an alkylidene group).

The alkenyl group may include vinyl, propenyl, isopropenyl and allyl groups or the like. The alkylidene group may include methylene, ethylidene, propylidene and isopropylidene groups or the like.

For example, when $R_1$ is a vinyl group or an ethylidene group, the compounds of formula (VI) may be represented by the following formulae (IV)-1, (IV)-2, (V)-1 and (V)-2:

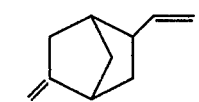

(IV)-1

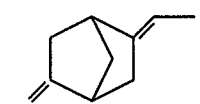

(IV)-2

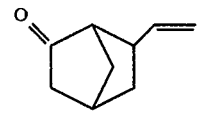

(V)-1 and

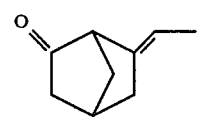

(V)-2

In accordance with the present invention, the alkenyl or alkylidene norbornanones represented hereinabove may be used singly or in a mixture of two or more.

The alkenyl norbornanones represented hereinabove may be prepared readily by adding an acid such as sulfuric acid, formic acid, acetic acid or the like to the alkenyl norbornenes such as vinyl norbornene; hydrolyzing the resulting products to give the alkenyl norboranols; and then oxidizing them to the alkenyl norbornanones. The alkenyl norbornene such as vinyl norbornene (5-vinyl-bicyclo [2.2.1] hept-2-ene) may be readily prepared on an industrial scale and at a low cost by means of the Diels-Alder reaction between cyclopentadiene and butadiene.

The alkylidene norbornanones represented hereinabove may be likewise prepared readily by adding an acid such as sulfuric acid, formic acid, acetic acid or the like to the alkylidene norbornenes such as ethylidene norbornene and hydrolyzing the resulting compounds; or by subjecting the alkylidene norbornenes to hydroboration-hydrogen peroxide oxidation to produce the corresponding ethylidene norbornanols; and then oxidizing the alcohols. It is to be noted, however, that the process including the step of adding the organic acid as mentioned hereinabove provides a large amount of tricyclene-type by-products which are less useful in perfumes, in addition to ethylidene norbornanol. These by-products are not readily separated by a usual distillation operation, so that it is preferable to produce ethylidene norbornanol by utilizing the hydroboration method.

The ethylidene norbornene (5-ethylidenebicyclo[2,2,1]hept-2-ene) can be readily prepared on an industrial scale and at a low cost as a third copolymeric component for EP rubber by isomerization of the vinyl norbornene represented hereinabove.

The diols to be used for the process in accordance with the present invention to convert the alkenyl or alkylidene norbornanones to the corresponding acetals may be a 1,2-diol or a 1,3-diol.

The term "1,2-diol" referred to herein means a compound in which two hydroxyl groups are attached respectively to two adjacent carbon atoms of a saturated hydrocarbon. The term "1,3-diol" referred to herein means a compound in which two hydroxyl groups are attached respectively to two carbon atoms of a saturated hydrocarbon, with another carbon atom interposed between the said carbon atoms.

Representatives of the 1,2-diols stated hereinabove may be ethylene glycol, 1,2-propanediol, 1,2-butanediol, 1,2-, 2,3- or 3,4-hexanediol, 1,2- or 2,3-pentanediol, 1,2-cyclohexanediol, 1,2-methylcyclohexanediol and the like.

Illustrative of the 1,3-diols may be 1,3-propanediol, 1,3-butanediol, 2,2-dimethyl-1,3-propanediol, 2,2-diethyl-1,3-propanediol, 2-methyl-1,3-propanediol, 2-ethyl-1,3-propanediol, 1,3-cyclohexanediol, 1,3-methylcyclohexanediol and the like.

In the reaction in which the corresponding acetals are formed, the diols represented hereinabove may be used singly or in a mixture.

When the diols are represented by the formula:

HO—$R_2$—OH, the process in accordance with the present invention may be represented by the following steps:

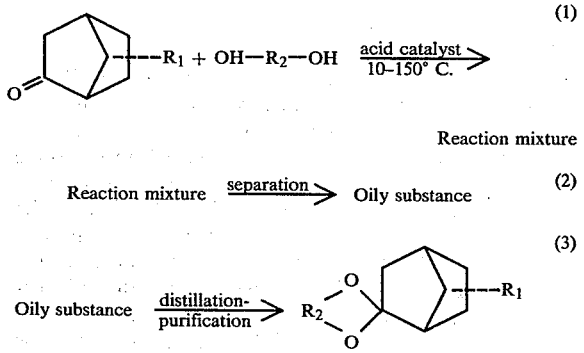

The reaction in the step (1) to be carried out in the presence of an acid catalyst involves a risk when carrying out the reaction at high temperatures using a large amount of a strong acid catalyst, because the unsaturated hydrocarbon group $R_1$ should not undergo any transformation. Thus, it is necessary to choose a reaction condition which does not cause polymerization.

The acid catalysts may include, for example, sulfuric acid, hydrochloric acid, hydrobromic acid, hydrofluoric acid, fluorosulfonic acid, chlorosulfonic acid, methanesulfonic acid, toluenesulfonic acid, boron fluoride hydrate, phosphoric acid, polyphosphoric acid, trichloroacetic acid, trifluoroacetic acid, perfluoroaliphatic acid, a strong-acid ion exchange resin, anhydrous phosphoric acid, anhydrous boric acid, acid clay and the like. Furthermore, the acid catalyst may be employed singly or in a mixture of two or more. However, care should be taken to avoid the use of a compound, such as boron fluoride, aluminum chloride, iron chloride, anhydrous sulfuric acid, very strong acids and so on in an anhydrous reaction system, which may cause a side-reaction. In order to carry out the reaction in the step (1) above, the reaction temperature is in the range of 10° C. to 150° C., preferably 30° C. to 100° C., and more preferably, 60° C. to 90° C. When the reaction temperature is below 10° C., the reaction requires a large amount of the acid catalyst and a long period of reaction time, thereby causing side-reactions other than the acetal formation and producing a large amount of, for example, polymerized products, and consequently descreasing the yield of the desired product. When the reaction is carried out at a temperature of higher than 150° C., the addition of the acid catalyst to the unsaturated hydrocarbon group $R_1$ takes place, thereby reducing the yield of the desired product.

The reaction of step (1), acetalization, requires removing the by-produced water to accelerate the acetal reaction.

Accordingly, it is preferred to carry out the acetal reaction under reflux with a solvent which can form a minimum boiling azeotrope with water and is inert in the acetal reaction. Such solvents may include, for example, benzene or toluene. It is also preferred to employ a solvent in order not to cause any conversion of the unsaturated bond during the acetal reaction.

In the process for preparing the norbornanone acetals in accordance with the present invention, the molar ratio of the alkenyl or alkylidene norbornanone to the diol to be used for the acetal formation is in the range of 1:0.5 to 1:3, and preferably, 1:1 to 1:2.

The amount of the acid catalyst represented hereinabove to be used in the acetal formation is in the range of 0.01 to 10% by weight, and preferably, 0.5 to 5% by weight with respect to the raw materials in the reaction system.

The reaction in the step (1) permits easy separation of the acetal from the reaction mixture when a usual alkanol (monoalcohol) is employed. However, the use of the diols as mentioned in the present invention requires some improvement or modification to isolate the desired product. The steps of acquiring the desired compound are represented by the steps (2) and (3) above. The oily substance of the step (2), which is a crude product, is first separated from the reaction mixture obtained in the step (1) under as moderate reaction conditions as possible. For this purpose, the separation may be carried out by extraction with an organic solvent from a mixture of the reaction mixture in water, by salting out, or by decantation, solution separation or centrifugation of a mixture of the reaction mixture in a solvent (such as water, ethylene glycol, Freon or the like) which does not completely dissolve the reaction mixture. When non-oily materials such as crystalline substances, rubbery substances or resinous substances are mixed in the reaction product during the course of separation, they must be removed as much as possible. It is appropriate that other non-oily materials such as water, organic solvents soluble in water, and so on may be removed by drying, evaporation, concentration of adsorption procedures. The oily substance thus obtained is then purified by distillation purification as represented in the step (3). Purification procedures other than distillation procedures cannot improve the quality of the desired product and decrease its yield. Accordingly, in order to facilitate purification by atmospheric-pressure distillation, reduced-pressure distillation, molecular distillation or the like, it is necessary to choose an appropriate raw material diol. Where purification by distillation cannot be effected because the desired product solidifies or is rendered waxy due to the use of a large molecular-weight diol, the separation of impurities cannot be accomplished. Thus, due attention should be paid to the choice of the raw material. In many cases, the method for purification by distillation is reduced-pressure fractional distillation (reduced pressure rectification). When the distillation results in complete purification, the alkenyl norbornanone acetals in accordance with the present invention may be obtained as colorless, transparent liquids.

The alkenyl or alkylidene norbornanone acetals in accordance with the present invention prepared as described hereinabove may be represented by the general formula (I) above. The acetal formation using the 1,2-diol results in the formation of the 1,3-dioxolane ring; that using the 1,3-diol results in the formation of the 1,3-dioxane ring.

Thus, the acetal formation from 5-vinyl-2 or 3-norbornanone and ethylene glycol results in the formation of vinylnorbornanone ethyleneacetal {2-(5-vinyl-norborn-2' or 3'-yl)-1,3-dioxolane} represented by the following formula:

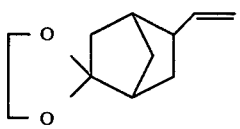
(II)-1 or

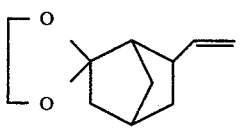
(III)-1

Since the carbon atom to which the alkenyl group such as the vinyl group or the like is attached has a hydrogen atom, there are two kinds of stereoisomers, the exo and endo-forms. They may be represented for the above 5-vinyl-2-norbornanone ethyleneacetal as follows:

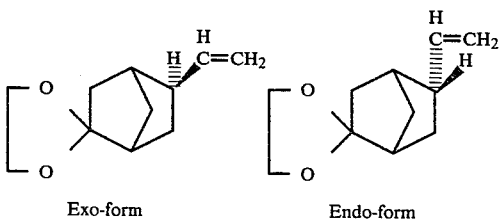

Exo-form    Endo-form

The acetal formation from 5-ethylidene-2 or 3-norbornanone and ethylene glycol results in the formation of ethylidene norbornanone ethyleneacetal or spiro[1,3-dioxolane-2,2' or 2,3'-(5'-ethylidenenorbornane)] represented by the following formula:

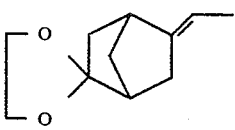
(II)-2 or

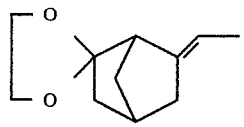
(III)-2

The alkenyl or alkylidene norbornanone acetals in accordance with the present invention are useful as perfume compositions because they have a desirable fragrance. Since the unsaturated groups such as the vinyl group or the ethylidene group can be utilized for further synthetic reactions, they can be used as useful intermediate products or raw materials for synthetic resins in the synthetic chemical industry.

Since the enthylidene norbornene is obtainable in a large amount and at a low cost as a third copolymeric monomer of EP rubber as stated hereinabove, it is economically advantageous to use as a starting material ethylidene norbornanone resulting from the oxidation of this ethylidene norbornene with the aid of the hydroboration method. This starting material does not contain any tricyclene-type compounds therein so that its usefulness in a perfume can be further enhanced.

Since vinyl norbornene is readily and cheaply available as an intermediate product for the manufacture of ethylidene norbornene for use in EPDM, it is economically advantageous to employ it as a starting material for the alkenyl norbornanone obtainable by acid addition, hydrolysis and oxidation.

Although the norbornene-type compounds in accordance with the present invention have a woody fragrance as a keynote, they may be favorably formulated with floral notes, fougere notes, mossy notes, chypre notes, leather notes, tobacco notes, animal notes, citrus notes, resinous notes, green notes, fruity notes, aldehydic notes, ester notes or the like to thereby provide various favorable perfume compositions. The perfume compositions may be employed as agents for providing fragrance in various perfumes, cosmetics, soaps, household products or the like. They may also be used extensively as flavor components, artificial essential oil components, deodorant components, perfume extender or the like.

The following examples illustrate the present invention in more detail.

Preparation Example 1

Synthesis of 5-vinyl-2 or 3-norbornanone

One mole of 5-vinyl-2-norbornene (5-vinyl-bicyclo-[2.2.1]hept-2-ene) was mixed with 4 moles of 98% formic acid and the mixture was stirred at 50°-70° C. for 4 hours. The unreacted formic acid was first recovered by reduced pressure distillation and then an ester having a boiling point of 104°-105° C./22 mmHg, $n_D^{14} = 1.4821$ (2- or 3-formoxy-5-vinylnorbornene) was obtained in a yield of about 62%.

One mole of the resulting ester and 1.2 moles of sodium hydroxide (used as a 10% aqueous solution) were mixed with methanol and the mixture was boiled for 2 hours to yield a reaction mixture which in turn was saturated with salt and then extracted with an etherbenzene mixture. The extract was dried over anhydrous magnesium sulfate and subjected to precision distillation to give an alcohol (5-vinyl-2 or 3-norbornanol)

having a boiling point of 85° C./4 mmHg, $n_D^{14} = 1.5020$ in a yield of over 90%.

A sulfuric acid solution of chromium trioxide was prepared by dissolving 5.6 g (0.056 mole) of chromium trioxide in 8 ml of water, adding 86 g (0.088 mole) of concentrated sulfuric acid to the solution while cooling it in an ice bath and then diluting the mixture with 16 ml of water. This solution was then added dropwise over a period of 30 minutes to an acetone solution of 31.6 g (0.23 mole) of the resulting alcohol while the solution was maintained at a temperature below 5° C. and stirred. The mixture was stirred at a temperature below 20° C., and then the resulting reaction mixture was treated by addition thereto of sodium hydrogen sulfite to form two separate layers. The lower layer was extracted with petroleum ether, and the petroleum ether layer was then combined with the upper layer previously obtained. The combined layers were washed with alkali hydroxide and then with water, and were distilled after being dried over anhydrous magnesium sulfate, thereby affording a ketone (5-vinyl-2 or 3-norbornanone) having a boiling point of 47°–48° C./0.35 mmHg in a yield of 77%.

The resultant ketone was analyzed by vapor phase chromatography (column filler: Silicone SE-30; column dimensions: 90 m in length and 0.25 m in diameter; stainless steel; column temperature, 150° C.). The analysis revealed that the resultant ketone was a mixture of 5-vinyl-2-norbornanone and 5-vinyl-3-norbornanone in a ratio of the former to the latter of about 70:30. The subsequent acetal formation did not change the ratio of the position isomers.

ir(neat method):

A strong absorption peak at 1,750 cm$^{-1}$ (stretching vibration of >C=O) appeared, and the stretching vibrations of C—O (1,000–1,110 cm$^{-1}$) and O—H of the alcohol (~3,400 cm$^{-1}$) disappeared.

nmr:
  4.0–4.6 $\tau$ (multiplet, 1H),
  4.8–5.2 $\tau$ (multiplet, 2H),
  7.0–8.6 $\tau$ (multiplet, 8H).

$n_D^{15}$: 1.4930

Elemental Analysis (as $C_9H_{12}O$):

|  | C(%) | H(%) |
|---|---|---|
| Calculated: | 79.43 | 8.82 |
| Found: | 79.40 | 8.89 |

Preparation Example 2

Synthesis of 5-ethylidene-2 and 3-norbornanones 5-Ethylidene-2-norbornene, 36.0 g (0.300 mole) was dissolved in 250 ml of dry tetrahydrofuran, and 5.0 g (0.129 mole) of sodium borohydride was added thereto. Boron trifluoride, 14.0 ml (0.111 mole) ether complex was dropwise added over about 30 minutes to the solution, while it was cooled in an ice bath. The mixture was thereafter stirred at 10°–20° C. for about 2 hours. To the resulting reaction mixture which was cooled with ice were added 25.2 ml of water and 34.1 ml of 3 N sodium hydroxide aqueous solution, and then gradually 34.1 ml of a 30% hydrogen peroxide aqueous solution was dropwise added. The resultant reaction mixture was stirred at about 50° C. for 2 hours and poured into 100 ml of a benzene-ether mixture. The mixture was washed several times with small amounts of saturated salt aqueous solution. The separated organic layer was dired over anhydrous magnesium sulfate, and the solvent was distilled off to afford residual materials which in turn were distilled under reduced pressure to given colorless 5-ethylidene-2 or 3-norbornanol (yield: 24.8 g, 60%, b.p., 60°–61° C./0.45 mmHg).

ir (neat method):
  ~3,300 cm$^{-1}$ (stretching vibration of O—H),
  ~1,680 cm$^{-1}$ (stretching vibration of C=C of ethylidene group),
  1,060–1,080 cm$^{-1}$ (stretching vibration of C—O of the alcohol)

nmr (CDCl$_3$):
  4.5–5.0 $\tau$ (multiplet, 1H),
  6.0–6.3 $\tau$ (multiplet, 1H),
  6.7 $\tau$ (singlet, 1H),
  7.2 $\tau$ (broad singlet, 1H),
  7.5–7.7 $\tau$ (multiplet, 1H),
  8.4 $\tau$ (singlet, 3H),
  7.9–8.9$\tau$ (multiplet, 6H).

Elemental Analysis (as $C_9H_{14}O$):

|  | C(%) | H(%) |
|---|---|---|
| Calculated: | 78.3 | 1.0 |
| Found: | 77.6 | 1.1 |

It was found from gas chromatography analysis that 95% of the resultant alcohol product was in the exo form, and 65% of the product was 5-ethylidene-2-norbornanol. No tricyclene-type compound was found at all.

A mixture of 5-ethylidene-2-norbornanol and 5-ethylidene-3-norbornanol, 5.0 g (0.036 mole) prepared above and 19.6 g (0.181 mole) of para-benzoquinone were dissolved in 160 ml of dry toluene.

Aluminum triisopropoxide, 3.7 g (0.018 mole) was gradually added at room temperature to the solution under stirring. After the reaction mixture was heated under reflux for 1 hour, 100 ml of sodium potassium tartarate saturated solution was added thereto and the mixture was extracted with a benzene-ether mixture. The extract was washed once with sodium hydrogen carbonate saturated solution and twice with water, and was distilled under reduced pressure after drying over anhydrous magnesium sulfate, leaving 4.2 g of 5-ethylidene-2 and 3-norbornanone (yield, 85%; b.p., 59°–60° C./1.8 mmHg).

ir (neat method):
  1,760 cm$^{-1}$ (stretching vibration of >C=O),
  ~1,685 cm$^{-1}$ (stretching vibration of C=C of ethylidene group).
  The stretching vibration of O—H (~3,400 cm$^{-1}$) was lost through oxidation.

nmr (CDCl$_3$):
  4.4–4.7 $\tau$ (multiplet, 0.6H),
  8.0–8.4 $\tau$ (multiplet, 8H),
  8.8–9.2 $\tau$ (quartet, 3H).

$n_D^{15}$: 1.4804.

Elemental Analysis (as $C_9H_{12}O$):

|  | C(%) | H(%) |
|---|---|---|
| Calculated: | 79.41 | 8.82 |
| Found: | 79.05 | 8.60 |

Gas chromatography analysis revealed that 5-ethylidene-2-norbornanone predominated, of which the exo form amounted to 95%.

EXAMPLE 1

Synthesis of spiro[1,3-dioxolane-2,2' or 2,3'-(5-vinylnorbornane)]

The ketone, 25 g (0.18 mole) prepared in Preparation Example 1 (5-vinyl-2 or 3-norbornanone), 14 g (0.22 mole) of ethylene glycol and a small amount of para-toluenesulfonic acid were added to 100 ml of benzene. The mixture was heated under reflux to remove the formed water by azeotropic distillation. After about 30 minutes, the reaction mixture was cooled to room temperature. The mixture was mixed with a small amount of anhydrous sodium carbonate and then stirred well. The resulting reaction mixture was washed with a small amount of water to remove most of the alkaline materials, and the benzene layer was dried over anhydrous magnesium sulfate. After benzene was distilled for removal, the residual materials were distilled under reduced pressure to give the acetal compound represented hereinabove as the title compound. The yield was 92% and the title compound was a colorless liquid which have green acrid camphorous order.

Boiling point:
 61°–62° C./0.7 mmHg.
$n_D^{23}$:
 1.4918.
ir (neat method):
 3,050 cm$^{-1}$ (stretching vibration of C—H of the vinyl group),
 1,630 cm$^{-1}$ (stretching vibration of C=C)
 The stretching vibration of C=O (1,730 cm$^{-1}$) was lost by conversion into acetal.
nmr (CDCl$_3$):
 3.8–4.5 $\tau$ (sextet, 1H),
 4.8–5.3 $\tau$ (multiplet, 2H),
 6.1 $\tau$ (singlet, 4H),
 7.2–8.7 $\tau$ (multiplet, 9H).
Elemental Analysis (as C$_{11}$H$_{16}$O$_2$)

|  | C(%) | H(%) |
|---|---|---|
| Calculated: | 73.3 | 8.9 |
| Found: | 73.5 | 8.5 |

The resultant spiro [1,3-dioxolane-2,2' or 2,3'-(5'-vinylnorbornane)] was formulated in the following composition to provide a base perfume in muguet (lily of the valley) note. The product can also be used as a component for Eau de Cologn having narcissus, lily-of-the-valley, lily, lilac or orange flower note.

| Phenylethyl alcohol | 260 g |
|---|---|
| phenylacetic acid | 25 g |
| Dimethylbenzyl carbinol | 25 g |
| α-Ionone | 75 g |
| Algerian jasmine absolute | 10 g |
| Benzyl acetate | 50 g |
| α-Amylcinnamic aldehyde | 60 g |
| Citral | 20 g |
| Aurantiol | 95 g |
| Heliotropin | 45 g |
| Linalool | 70 g |
| Vanillin | 10 g |
| 10% Indole ethanol solution | 30 g |
| Methyl Jasmonate | 40 g |
| Terpineol | 150 g |
| Acetal prepared above | 35 g |
| Total | 1,000 g |

EXAMPLE 2

Synthesis of spiro[4,5-dimethyl-1,3-dioxolane-2,2' or 2,3'-(5'-vinylnorbornane)]

The ketone prepared in Preparation Example 1 was converted into the corresponding acetal in the same manner as in Example 1 to give the title compound in a 78.7% yield.

Boiling point:
 83°–84° C./1.5 mm Hg.
$n_D^{23}$:
 1.4741
ir (neat method);
 3,052 cm$^{-1}$ (stretching vibration of C—H of vinyl group),
 1,630 cm$^{-1}$ (stretching vibration of C=C),
 The stretching vibration of >C=O (1,730 cm$^{-1}$) disappeared through conversion into acetal.
nmr (CDCl$_3$):
 3.5–4.6 $\tau$ (sextet, 1H),
 4.8–5.3 $\tau$ (multiplet, 2H),
 6.0–6.1 $\tau$ (quartet, 2H),
 7.1–8.7 $\tau$ (multiplet, 9H),
 8.8–9.0 $\tau$ (doublet, 6H).
Elemental Analysis (as C$_{13}$H$_{20}$O$_2$):

|  | C(%) | H(%) |
|---|---|---|
| Calculated: | 75.0 | 9.6 |
| Found: | 74.7 | 9.9 |

The resultant spiro[4,5-dimethyl-1,3-dioxolane-2,2' or 2,3'-(5'-vinylnorbornane)] was formulated in the following composition to provide a perfume in lavender note for use in soaps. The product can also be used in hair tonic for men by diluting it with refined alcohol.

| English lavender oil | 525 g |
|---|---|
| Bourbon bergamot oil | 80 g |
| Indonesian bois de rose oil | 100 g |
| Geranium oil | 50 g |
| Rcmarin oil | 50 g |
| Patchouli oil | 25 g |
| Coumarin | 40 g |
| Musk ketone | 30 g |
| Heliotropin | 50 g |
| Benzoic acid | 25 g |
| Acetal prepared above | 25 g |
| Total | 1,000 g |

EXAMPLE 3

Synthesis of spiro[1,3-dioxane-2,2' or 2,3'-(5'-vinylnorbornane)]

The ketone prepared in Preparation Example 1 was converted into the corresponding acetal with trimethylene glycol in the same manner as in Example 1 to give the title compound in a 79.7% yield.

Boiling point:
 98°–99° C./2.0 mmHg.
$n_D^{24}$:
 1.4984.
ir (neat method):
 3,050 cm$^{-1}$ (stretching vibration of C—H of vinyl group),
 1,630 cm$^{-1}$ (stretching vibration of C=C),
 The stretching vibration of >C=O (1,730 cm$^{-1}$) was lost in the actual conversion.

nmr (CDCl₃):
3.7–4.4 τ (sextet, 1H),
4.8–5.2 τ (multiplet, 2H),
6.1–6.2 τ (triplet, 4H)
7.0–8.8 τ (multiplet, 11H).
Elemental Analysis (as $C_{12}H_{18}O_2$):

|  | C(%) | H(%) |
|---|---|---|
| Calculated: | 74.2 | 9.3 |
| Found: | 73.8 | 9.5 |

The spiro[1,3-dioxane-2,2' or 2,3'-(5'-vinylnorbornane)] prepared hereinabove as formulated in the following composition to provide a perfume in fougere notes. This compound can also be used as a base for oriental perfumes for women.

| Madagascar terpeneless bergamot oil | 100 g |
|---|---|
| Linalool | 150 g |
| Mysore sandalwood oil | 100 g |
| Coumarin | 100 g |
| English orris oil | 60 g |
| Vanillin | 20 g |
| Musk ambrette | 20 g |
| Linalyl acetate | 70 g |
| Bulgarian rose absolute | 50 g |
| Musk ketone | 50 g |
| Acetal prepared hereinabove | 170 g |
| Total | 890 g |

EXAMPLE 4

Synthesis of spiro[5,5-dimethyl-1,3-dioxane-2,2' or 2,3'-(5'-vinylnorbornane)]

The ketone prepared in Preparation Example 1 was converted into the corresponding acetal with 2,2-dimethyl-1,3-propanediol in the same manner as in Example 1 to provide the title compound in a 75.8% yield.
Boiling point:
69°–70° C./0.25 mmHg,
$n_D^{24}$:
1.4841
ir (neat method):
3,060 cm⁻¹ (stretching vibration of C—H of vinyl group),
1,625 cm⁻¹ (stretching vibration of C=C),
The stretching vibration of >C=O (1,730 cm⁻¹) was lost in the acetal conversion.
nmr (CDCl₃):
3.7–4.5 τ (sextet, 1H),
4.7–5.2 τ (multiplex, 2H),
6.1 τ (singlet, 4H),
7.2–8.7 τ (multiplet, 9H),
9.0 τ (singlet, 6H).
Elemental Analysis (as $C_{14}H_{22}O_2$):

|  | C(%) | H(%) |
|---|---|---|
| Calculated: | 75.7 | 9.9 |
| Found: | 75.9 | 10.1 |

The spiro[5,5-dimethyl-1,3-dioxane-2,2' or 2,3'-(5'-vinylnorbornane)] prepared hereinabove was formulated in the following composition to provide a chypres base perfume. This base perfume can be used as a component of modern chypre notes for women's cosmetics.

| Madagascar terpeneless bergamot oil | 200 g |
|---|---|
| Fench rose absolute | 200 g |
| Methyl anthranilate | 50 g |
| Vanillin | 70 g |
| Heliotropin | 50 g |
| Phenylethyl alcohol | 100 g |
| Irone | 30 g |
| Acetal prepared hereinabove | 300 g |
| Total | 1,000 g |

EXAMPLE 5

Synthesis of spiro[4-methyl-1,3-dioxane-2,2' or 2,3'-(5'-vinylnorbornane)]

The ketone prepared in Preparation Example 1 was converted into the corresponding acetal with 1,3-butanediol in the same manner as in Example 1 to provide the title compound in a 70.4% yield.
Boiling point: 82–83° C./0.80 mmHg
$n_D^{23}$: 1.4887
ir (neat method);
3,050 cm⁻¹ (stretching vibration of C—H of vinyl group),
1,625 cm⁻¹ (stretching vibration of C=C)
The stretching vibration of >C=O (1,730 cm⁻¹) was lost in the acetal conversion.
nmr (CDCl₃):
3.8–4.5 τ (sextet, 1H),
4.7–5.2 τ (multiplet, 2H),
6.1–6.3 τ (multiplex, 3H),
7.1–8.6 τ (multiplet, 11H),
8.9 τ (doublet, 3H).
Elemental Analysis (as $C_{13}H_{20}O_2$):

|  | C(%) | H(%) |
|---|---|---|
| Calculated: | 75.0 | 9.6 |
| Found: | 74.6 | 9.5 |

The spiro[4-methyl-1,3-dioxane-2,2' or 2,3-(5'-vinylnorbornane)] prepared hereinabove was formulated in the following composition to provide a perfume in Oriental rose notes. This perfume can be used conveniently for various uses as a formulation base in the rose series.

| Perfume prepared in Example 1 | 150 g |
|---|---|
| α-Ionone | 25 g |
| Bulgarian rose oil | 50 g |
| Phenyl acetate | 5 g |
| Bourbon geranium oil | 50 g |
| Phenyl ethyl alcohol | 120 g |
| Rhodinol | 250 g |
| Mysore sandalwood oil | 10 g |
| Musk Tincture | 10 g |
| Mixed artificial musk oils | 100 g |
| Lavol, (3,6-dimethylocton-3-01) | 30 g |
| Acetal prepared hereinabove | 100 g |
| Total | 900 g |

EXAMPLE 6

Synthesis of spiro [5,5-diethyl-1,3-dioxane-2,2' or 2,3'-(5'-vinylnorbornane]

The ketone prepared in Preparation Example 1 was converted into the corresponding acetal with 2,2-diethyl-3-propanediol in the same manner as in Example 1 to provide the title compound in a 78.0% yield.

Boiling point:
77°–78° C./0.20 mmHg,
$n_D^{24}$:
1.4910,
ir (neat method):
- 3,050 cm$^{-1}$ (stretching vibration of C—H of vinyl group),
- 1,630 cm$^{-1}$ (stretching vibration of C=C),
- The stretching vibration of >C=O (1,730 cm$^{-1}$) was lost in the acetal conversion.

nmr (CDCl$_3$):
- 3.8–4.5 τ (sextet, 1H),
- 4.8–5.2 τ (multiplet, 2H),
- 6.1 τ (singlet, 4H),
- 7.2–8.7 τ (multiplet, 13H)
- 8.9–9.1 τ (triplet, 6H).

Elemental Analysis (as C$_{16}$H$_{26}$O$_2$):

|  | C(%) | H(%) |
|---|---|---|
| Calculated: | 76.8 | 10.4 |
| Found: | 76.4 | 10.3 |

The spiro[5,5-diethyl-1,3-dioxane-2,2′ or 2,3′-(5′-vinylnorbornane)] prepared hereinabove was formulated in the following composition to provide a perfume for soaps in violet note. This perfume is also useful as a base for rose-violet type formulated cosmetics.

| α-Ionone | 300 g |
|---|---|
| Methylionone | 100 g |
| α-Hexylcinnami aldehyde | 20 g |
| Benzyl acetate | 30 g |
| Benzyl alcohol | 100 g |
| Heliotropin | 100 g |
| French bergamot oil | 125 g |
| Moroccan rose absolute | 10 g |
| Phenylethyl alcohol | 140 g |
| Leaf alcohol, (cis-3-hexenol) | 5 g |
| Acetal prepared hereinabove | 70 g |
| Total | 1,000 g |

EXAMPLE 7

Synthesis of spiro[4,5-tetramethylene-1,3-dioxolane-2,2′ or 2,3′-(5′-vinylnorbornane)]

The ketone prepared in Preparation Example 1 was converted into the corresponding acetal with 1,2-cyclohexanediol in the same manner as in Example 1 to provide the title compound in a 64.1% yield.
Boiling point: 92°–94° C./0.02 mmHg,
$n_D^{24}$:
1.5028,
ir (neat method):
- 3,050 cm$^{-1}$ (stretching vibration of C—H of vinyl group),
- 1,625 cm$^{-1}$ (stretching vibration of C=C),
- The stretching vibration of >C=O (1,730 cm$^{-1}$ was lost in the acetal conversion.

nmr (CDCl$_3$):
- 3.7–4.3 τ (sextet, 1H),
- 4.7–5.3 τ (multiplet, 2H),
- 5.9–6.0 τ (triplet, 2H),
- 7.2–8.9 τ (multiplet, 17H).

Elemental Analysis (as C$_{15}$H$_{22}$O$_2$):

|  | C(%) | H(%) |
|---|---|---|
| Calculated | 76.9 | 9.4 |
| Found: | 77.2 | 9.3 |

The spiro[4,5-tetramethylene-1,3-dioxolane-2,2′ or 2,3′-(5′-vinylnorbornane)] was formulated in the following composition to provide a perfume in a kind of orchard cattleya note.

| Hydroxycitronellal | 150 g |
|---|---|
| Terpineol | 125 g |
| Madagascar ylang-ylang oil | 100 g |
| Phenylethyl alcohol | 70 g |
| Jasmone | 20 g |
| Linalool | 40 g |
| α-Amylcinnamic aldehyde | 20 g |
| Methylnonyl acetaldehyde | 10 g |
| Isobutyl aslicylate | 150 g |
| Benzyl salicylate | 25 g |
| Ethylvanillin | 10 g |
| Heliotropin | 20 g |
| Synthetic macro-ring ketone, (Exaltone) | 20 g |
| Coumarin | 40 g |
| α-Ionone | 50 g |
| Zanzibar bargamot oil | 100 g |
| Acetal prepared hereinabove | 50 g |
| Total | 1,000 g |

This perfume can be used as an atractive deodorant for use in room by mixing it with an aqueous gel of sodium polyacrylate. It can also be employed as a disinfectant-odorant for use in detergents by mixing it with methyl violet, a surfactant and polyethylene oxide to thereby shape a desired form.

EXAMPLE 8

Synthesis of spiro[1,3-dioxolane-2,2′ or 2,3′-(5′-ethylidene norbornane)]

The ketone prepared in Preparation Example 2 was converted into the corresponding acetal with ethylene glycol in the same manner as in Example 1 to provide the title compound, i.e., 5-ethylidenenorbornanone ethyleneacetal (2.1 g; yield, 63.5%; b.p., 61–62%/0.30 mmHg).
ir (neat method):
- ~1,690 cm$^{-1}$ (stretching vibration of C=C of ethylidene group),
- The stretching vibration of C=O (~1,750 cm$^{-1}$) was lost in the acetal conversion.

nmr (CDCl$_3$):
- 4.6–5.0 τ (multiplet, 1H)
- 6.2 τ (singlet, 4H)
- 7.5 τ (broad singlet, 1H)
- 7.6–7.8 τ (multiplet 1H)
- 8.4 τ (singlet, 3H)
- 7.9–9.0 τ (multiplet, 6H)

Elemental Analysis (as C$_{11}$H$_{16}$O$_2$):

|  | C(%) | H(%) |
|---|---|---|
| Calculated: | 73.3 | 8.9 |
| Found: | 73.8 | 8.7 |

The spiro[1,3-dioxolane-2,2′ and 2,3′ (5′-ethylidenenorbornane)] was formulated in the following composition to provide a perfume composition useful as a base for a lily fragrance. This composition can be used as a perfume for soaps.

| | |
|---|---|
| phenylethyl alcohol | 10.9 g |
| Benzyl alcohol | 10.9 g |
| Dimethylbenzyl carbinol | 3.3 g |
| β-Ionone | 6.6 g |
| Benzyl acetate | 5.5 g |
| α-Amylcinnamic aldehyde | 6.6 g |
| Citral | 1.6 g |
| Aurantiol | 4.4 g |
| Heliotropin | 2.2 g |
| Linalool | 25.0 g |
| Musk xylene | 3.3 g |
| 10% Indole methanol solution | 3.3 g |
| Methyl jasmonate | 4.4 g |
| Terpineol | 8.2 g |
| Acetal prepared hereinabove | 3.8 g |
| Total | 100 g |

EXAMPLE 9

Synthesis of spiro[4,5-dimethyl-1,3-dioxolane-2,2' and 2,3'-(5'-ethylidene norbornane)]

The ketone (5-ethylidene-2 and 3-norbornanone) prepared in Preparation Example 2 was converted into the corresponding acetal with 2,3-butanediol in the same manner as in Example 1 to provide the title compound in a 70.0% yield.
b.p.: 68°–70° C/0.6 mmHg,
$n_D^{23}$:
  1.4692
ir (neat method):
  1,640 cm$^{-1}$ (stretching vibration of C=C of ethylidene group)
  The stretching vibration of >C=O (1,730 cm$^{-1}$) was lost by the acetal formation
nmr (CDCl$_3$):
  4.6–5.1 τ (multiplet, 1H)
  6.0–6.1 τ (quartet, 2H)
  7.4–8.7 τ (multiplet, 8H)
  8.4 τ (singlet, 3H)
  8.8–9.0 τ (doublet, 6H)
Elemental Analysis (as C$_{13}$H$_{20}$O$_2$):

| | C(%) | H(%) |
|---|---|---|
| Calculated: | 75.0 | 9.6 |
| Found: | 74.5 | 9.8 |

The spiro[4,5-dimethyl-1,3-dioxolane-2,2' and 2,3'-(5'-ethylidenenorbornane)] was formulated in the following composition to provide a perfume in lavender note for use in soaps. This can also be used as a base perfume for men's cologne.

| | |
|---|---|
| Lavender oil | 47.2 g |
| Bergamot oil | 9.4 g |
| Bois de rose oil | 11.8 g |
| Geranium oil | 5.9 g |
| Petitgrain oil | 2.9 g |
| Patchouli oil | 2.9 g |
| Coumarin oil | 4.7 g |
| Musk ketone | 3.5 g |
| Heliotropin | 5.9 g |
| Vanillin | 2.9 g |
| Acetal prepared hereinabove | 2.9 g |
| Total | 100 g |

EXAMPLE 10

Synthesis of spiro[1,3-dioxane-2,2' and 2,3'-(5'-ethylidenenorbornane)]

The ketone (5-ethylidene-2 and 3-norbornanone) prepared in Preparation Example 2 was converted into the corresponding acetal with trimethylene glycol in the same manner as in Example 1 to provide the title compound in an 80% yield.
b.p.:
  72° C./0.40 mmHg
$n_D^{24}$:
  1.4831
ir (neat method):
  1,640 cm$^{-1}$ (stretching vibration of C=C of ethylidene group)
  The stretching vibration of C=O (1,730 cm$^{-1}$) was lost in the acetal conversion.
nmr (CDCl$_3$):
  4.5–5.0 τ (multiplet, 1H),
  6.1–6.2 τ (triplet, 4H),
  8.4 τ (singlet, 3H),
  7.2–8.8 τ (multiplet, 10H).
Elemental Analysis (as C$_{12}$H$_{18}$O$_2$):

| | C(%) | H(%) |
|---|---|---|
| Calculated | 74.2 | 9.3 |
| Found | 73.8 | 9.5 |

The spiro[1,3-dioxane-2,2' and 2,3'-(5'-ethylidene norbornane)] prepared hereinabove was formulated in the following composition to provide a perfume in floral-fougere note. This can be used as a base for fragrant gel perfumes for use in rooms.

| | |
|---|---|
| Bergamot oil | 10.0 g |
| Phenylethyl alcohol | 11.0 g |
| Linalool | 11.0 g |
| Linalyl acetate | 4.0 g |
| Sandalwood oil | 10.0 g |
| Heliotropin | 5.0 g |
| Coumarin | 5.0 g |
| Orris oil | 6.0 g |
| Vanillin | 2.0 g |
| Musk ambrette | 2.0 g |
| Linalyl benzoate | 7.0 g |
| Rose absolute | 5.0 g |
| Macro-ring ketone (TMII-SP, 5-cyclohexadecenone) | 5.0 g |
| Acetal prepared hereinabove | 17.0 g |
| Total | 100 g |

EXAMPLE 11

Synthesis of spiro[5,5-dimethyl-1,3-dioxane-2,2' and 2,3'-(5'-ethylidene norbornane)]

The ketone (5-ethylidene-2 and 3-norbornanone) prepared in Preparation Example 2 was converted into the corresponding acetal with 2,2-dimethyl-1,3-propanediol in the same manner as in Example 1 to provide the title compound in a 65.5% yield.
b.p.:
  108°–109° C./3.0 mmHg,
$n_D^{24}$:
  1.4755,
ir (neat method):
  1,635 cm$^{-1}$ (stretching vibration of C=C of ethylidene group)

The stretching vibration of >C=O (1,730 cm⁻¹) was lost by the acetal formation.

nmr (CDCl₃):
4.5–5.1 τ (multiplet, 1H),
6.1 τ (singlet, 4H),
8.3 τ (singlet, 3H)
7.3–8.7 τ (multiplet, 8H),
9.0 τ (singlet, 6H), Elemental Analysis (as $C_{14}H_{22}O_2$):

|  | C(%) | H(%) |
|---|---|---|
| Calculated: | 75.7 | 9.9 |
| Found: | 75.8 | 10.0 |

The spiro[5,5-dimethyl-1,3-dioxane-2,2' and 2,3'-(5'-ethylidenenorbornane)] prepared hereinabove was formulated in the following composition to provide a cypress base aerosol pack perfume of chypre type eau de toilette.

| Bergamot oil | 20.8 g |
|---|---|
| Rose absolute | 9.4 g |
| Zdrabetz oil | 1.0 g |
| Methyl anthranilate | 5.2 g |
| Terpineol | 7.3 g |
| Vanillin | 7.3 g |
| Ambrette | 3.1 g |
| Heliotropin | 5.2 g |
| Methylionone | 1.0 g |
| Phenylethyl alcohol | 7.3 g |
| Phenylethyl acetate | 3.1 g |
| Irone | 3.1 g |
| Acetal prepared hereinabove | 26.2 g |
| Total | 100 g |

EXAMPLE 12

Synthesis of spiro[4-methyl-1,3-dioxane-2,2' and 2,3'-(5'-ethylidenenorbornane)]

The ketone(5-ethylidene-2 and 3-norbornanone) prepared in Preparation Example 2 was converted into the corresponding acetal with 1,3-butanediol in the same manner as in Example 1 to provide the title compound in a 70% yield.

b.p.:
82°–83° C./0.65 mmHg
$n_D^{24}$:
1.4898 ir (neat method):
1,635 cm⁻¹ (stretching vibration of C=C of ethylidene group),
The stretching vibration of >C=O (1,730 cm⁻¹) was lost by the acetal formation.

nmr (CDCl₃):
4.6–5.0 τ (multiplet, 1H),
6.1–6.3 τ (multiplet, 3H),
8.5 τ (singlet, 3H),
7.3–8.8 τ (multiplet, 10H), 8.9 τ (doublet, 3H).

Elemental Analysis (as $C_{13}H_{20}O_2$):

|  | C(%) | H(%) |
|---|---|---|
| Calculated: | 75.0 | 9.6 |
| Found: | 74.7 | 9.8 |

The spiro[4-methyl-1,3-dioxane-2,2' and 2,3'-(5'-ethylidenenorbornane)] prepared hereinabove was formulated in the following composition to provide a perfume in oriental rose notes. This perfume can be conveniently used for various purposes as a roseous base.

Perfume according to the formulation of

| Example 1 | 10.6 g |
|---|---|
| Methylionone | 2.1 g |
| Rose absolute | 3.2 g |
| Zdrabetz oil | 2.1 g |
| Phenyl acetic acid | 0.5 g |
| Geranium oil | 6.4 g |
| Phenylethyl alcohol | 16.0 g |
| Aurantiol | 2.1 g |
| Rhodinol | 26.6 g |
| Dimethylbenzyl carbinol | 3.2 g |
| Sandalwood oil | 1.1 g |
| Tonquin musk tincture | 1.1 g |
| Mixed artificial must oil | 10.1 g |
| Benzyl salicylate | 4.3 g |
| Acetal prepared hereinabove | 10.6 g |
| Total | 100 g |

EXAMPLE 13

Synthesis of spiro[5,5-diethyl-1,3-dioxane-2,2' and 2,3'-(5'-ethylidenenorbornane)]

The ketone (5-ethylidene-2 and 3-norbornanone) prepared in Preparation Example 2 was converted into the corresponding acetal with 2,2-diethyl-1,3-propanediol in the same manner as in Example 1 to provide the title compound in a 68% yield.

b.p:
75°–77° C./0.20 mmHg,
$n_D^{24}$:
1.4835 ir (neat method):
1,640 cm⁻¹ (stretching vibration of C=C of ethylidene group), The stretching vibration of >C=O (1.730 cm⁻¹) was lost by the acetal formation.

nmr (CDCl₃):
4.5–5.0 τ (multiplet, 1H),
6.1 τ (singlet, 4H),
8.4 τ (singlet, 3H),
7.3–8.9 τ (multiplet, 12H),
8.9–9.1 τ (triplet, 6H).

Elemental Analysis (as $C_{16}H_{26}O_2$):

|  | C(%) | H(%) |
|---|---|---|
| Calculated: | 76.8 | 10.4 |
| Found: | 76.2 | 10.1 |

The spiro[5,5-diethyl-1,3-dioxane-2,2' and 2,3'-(5'-ethylidenenorbornane)] was formulated into the following composition to provide a perfume for a detergent with violet notes.

| α-Ionone | 27.5 g |
|---|---|
| Methylionone | 9.2 g |
| α-Hexylcinnamic aldehyde | 1.8 g |
| Dihydrojasmine acid methyl ester | 1.8 g |
| Benzyl alcohol | 9.2 g |
| Heliotropin | 9.2 g |
| Bergamot oil | 11.5 g |
| Benzyl salicylate | 4.6 g |
| Rose absolute | 0.9 g |
| Phenylethyl alcohol | 12.8 g |
| Leaf alcohol, (cis-3-hexenol) | 0.5 g |
| Acetal prepared hereinabove | 11.0 g |
| Total | 100 g |

EXAMPLE 14

Synthesis of spiro[4,5-tetramethylene-1,3-dioxolane-2,2 and 2,3-(5'-ethylidenenorbornane)]

The ketone (5-ethylidene-2 and 3-norbornanone) prepared in Preparation Example 2 was converted into the corresponding acetal with 1,2-cyclohexanediol in the same manner as in Example 1 to provide the title compound in a 60.5% yield.

b.p.:
92°–94° C./0.35 mmHg, $n_d^{24}$:
1.4950, ir (neat method):
1,635 cm$^{-1}$ (stretching vibration of C=C of ethylidene group),
The stretching vibration of >C=O (1,730 cm$^{-1}$) was lost by the acetal formation.

nmr (CDCl$_3$):
4.6–5.0 τ (multiplet, 1H),
5.9–6.0 τ (triplet, 2H),
8.3 τ (singlet, 3H),
7.3–8.9 τ (multiplet, 16H).

Elemental Analysis (as $C_{15}H_{22}O_2$):

|  | C(%) | H(%) |
|---|---|---|
| Calculated: | 76.9 | 9.4 |
| Found: | 77.1 | 9.2 |

The spiro[4.5-tetramethylene-1,3-dioxolane-2,2' and 2,3'-(5'-ethylidenenorbornane)] prepared hereinabove was formulated into the following composition to provide a floral bouquet perfume which may be used as a component for a deodorant, malodour masking agent, or as an agent for imparting a fragrance to household products.

| Hydroxycitronellal | 10.3 g |
|---|---|
| Terpineol | 12.8 g |
| Ylang-ylang oil | 10.3 g |
| Jasmone | 2.1 g |
| Phenylethyl alcohol | 10.3 g |
| Linalool | 6.2 g |
| α-Amylcinnamic alhehyde | 3.1 g |
| Methylnonyl acetaldehyde | 1.0 g |
| Isoamyl salicylate | 10.3 g |
| Benzyl salicylate | 2.6 g |
| Lily aldehyde | 1.0 g |
| Ethylvanillin | 1.0 g |
| Heliotropin | 2.1 g |
| Synthetic macro-ring ketone, (5-cyclohexadecenone) | 2.1 g |
| Coumarin | 4.1 g |
| α-Ionone | 5.2 g |
| Bergamot oil | 10.3 g |
| Acetal prepared hereinabove | 5.2 g |
| Total | 100 g |

EXAMPLE 15

Synthesis of sprio[1,3-dioxolane-2,2' and 2,3'-(5'-isopropylidenenorbornane)]

5-Isopropylidene-2-norbornene was treated in the same manner as in Preparation Example 2 to give 5-isopropylidene-2 and 3-norbornanol which was oxidized to the ketone. The ketone was converted into the corresponding acetal with ethylene glycol in the same manner as in Example 1 to provide the title compound in a 65% yield.

b.p.:
65°–67° C./0.60 mmHg, $n_D^{24}$:
1.4820 ir (neat method):
1,665 cm$^{-1}$ (weak absorption, stretching vibration of C=C of isopropylidene group) The stretching vibration of >C=O (1,730 cm$^{-1}$) was lost by the acetal formation.

nmr (CDCl$_3$):
6.1 τ (singlet, 4H),
7.4 τ (broad singlet, 1H),
8.3 τ (singlet, 3H),
8.4 τ (singlet, 3H),
7.9–8.8 τ (multiplet, 7H), Elemental Analysis (as $C_{12}H_{18}O_2$):

|  | C(%) | H(%) |
|---|---|---|
| Calculated: | 74.2 | 9.3 |
| Found: | 73.5 | 9.5 |

The spiro[1,3-dioxolane-2,2' and 2,3'-(5'-isopropylidenenorbornane)] prepared hereinabove was formulated in the following composition to provide a floral perfume composition in lavender fougere note for use in soaps.

| Lavender oil | 17.9 g |
|---|---|
| Geranium oil | 7.1 g |
| Oak moss resinoid | 3.6 g |
| α-Ionone | 4.4 g |
| Coumarin | 5.4 g |
| Patchouli oil | 4.5 g |
| Cedarwood oil | 13.4 g |
| Sandalwood oil | 3.6 g |
| Vetiver oil | 0.9 g |
| Terpinyl acetate | 11.6 g |
| Benzyl salicylate | 8.0 g |
| Rhodinol | 8.9 g |
| Musk ambrette | 4.5 g |
| Labdanum resinoid | 1.8 g |
| Acetal prepared hereinabove | 4.4 g |
| Total | 100 g |

What is claimed is:

1. A compound represented by the general formula:

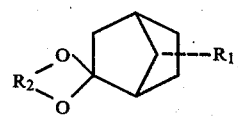

(I)

(wherein R$_1$ is an alkenyl group having 2 or 3 carbon atoms or an alkylidene group having 1 to 3 carbon atoms and R$_2$ is the saturated hydrocarbon group having 2 to 7 carbon atoms, with a dotted line between the two carbon atoms indicating a single bond when R$_1$ is an alkenyl group and a double bond when R$_1$ is alkylidene group).

2. The compound according to claim 1, wherein the compound is represented by the general formula (II)-1, (II)-2, (III)-1 or (III)-2:

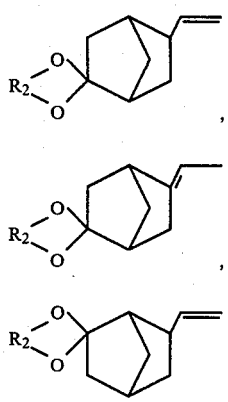

or

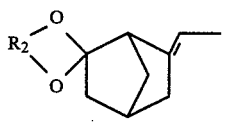

(wherein $R_2$ is a saturated hydrocarbon group having 2 to 7 carbon atoms).

3. The compound according to claim 2, wherein the compound is spiro[1,3-dioxolane-2,2' or 2,3'-(5'-vinylnorbornane)].

4. The compound according to claim 2, wherein the compound is spiro[4,5-dimethyl-1,3-dioxolane-2,2' or 2,3'-(5'-vinylnorbornane)].

5. The compound according to claim 2, wherein the compound is spiro[1,3-dioxane-2,2' or 2,3'-(5'-vinylnorbornane)].

6. The compound according to claim 2, wherein the compound is spiro[5,5-dimethyl-1,3-dioxane-2,2' or 2,3'-(5'-vinylnorbornane)].

7. The compound according to claim 2, wherein the compound is spiro[4-methyl-1,3-dioxane-2,2' or 2,3'-(5'-vinylnorbornane)].

8. The Compound according to claim 2, wherein the compound is spiro[5,5-diethyl-1,3-dioxane-2,2' or 2,3'-(5'-vinylnorbornane)].

9. The compound according to claim 2, wherein the compound is spiro[4,5-tetramethylene-1,3-dioxolane-2,2' or 2,3'-(5'-vinylnorbornane)].

10. The compound according to claim 2, wherein the compound is spiro[1,3-dioxolane-2,2' or 2,3'-(5'-ethylidenenorbornane)].

11. The compound according to claim 2, wherein the compound is spiro[4,5-dimethyl-1,3-dioxolane-2,2' or 2,3'-(5'-ethylidenenorbornane)].

12. The compound according to claim 2, wherein the compound is spiro[1,3-dioxane-2,2' or 2,3'-(5'-ethylidenenorbornane)].

13. The compound according to claim 2, wherein the compound is spiro[5,5-dimethyl-1,3-dioxane-2,2' or 2,3'-(5'-ethylidenenorbornane)].

14. The compound according to claim 2, wherein the compound is spiro[4-methyl-1,3-dioxane-2,2' or 2,3'-(5'-ethylidenenorbornane)].

15. The compound according to claim 2, wherein the compound is spiro[5,5-diethyl-1,3-dioxane-2,2' or 2,3'-(5'-ethylidenenorbornane)].

16. The compound according to claim 2, wherein the compound is spiro[4,5-tetramethylene-1,3-dioxolane-2,2' or 2,3'-(5'-ethylidenenorbornane)].

17. A perfume composition containing as a perfume active constituent a compound of the general formula (I):

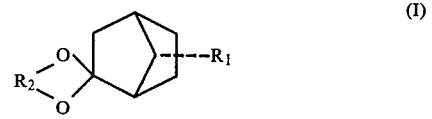

(wherein $R_1$ is an alkenyl group having 2 or 3 carbon atoms or an alkylidene group having 1 to 3 carbon atoms and $R_2$ is a saturated hydrocarbon group having 2 to 7 carbon atoms, with the dotted line between the two carbon atoms indicating a single bond when $R_1$ is an alkenyl group and a double bond when $R_1$ is an alkylidene group and a conventional adjuvant).

18. The perfume composition according to claim 17, wherein the compound is represented by general formula (II)-1, (II)-2, (III)-1 or (III)-2:

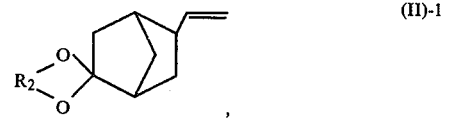

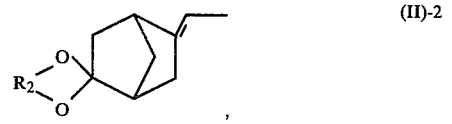

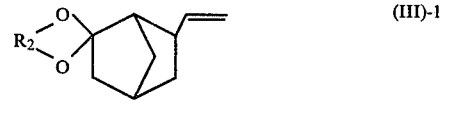

or

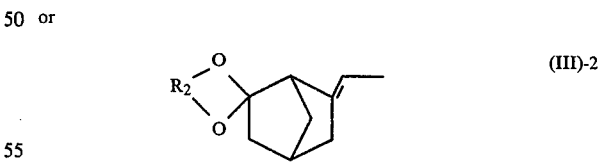

(wherein $R_2$ is a saturated hydrocarbon group having 2 to 7 carbon atoms).

* * * * *